United States Patent [19]

Andersson et al.

[11] Patent Number: 5,192,173
[45] Date of Patent: Mar. 9, 1993

[54] COPYING METHOD AND DEVICE

[75] Inventors: Matts Andersson, Fåker; Värne Gustavsson, Karlskoga, both of Sweden

[73] Assignee: Nobelpharma AB, Gothenburg, Sweden

[21] Appl. No.: 483,725

[22] Filed: Feb. 23, 1990

[30] Foreign Application Priority Data

Feb. 23, 1989 [SE] Sweden .............................. 8900621

[51] Int. Cl.$^5$ .......................................... B23Q 35/10
[52] U.S. Cl. ...................................... 409/84; 409/86; 409/88
[58] Field of Search .............. 409/123, 94, 104, 111, 409/122, 84, 127, 85, 86, 87, 88, 89, 92; 82/11, 11.3, 12

[56] References Cited

U.S. PATENT DOCUMENTS

| | | | |
|---|---|---|---|
| 361,131 | 4/1887 | Carlinet | 409/86 |
| 888,041 | 5/1908 | Salo | 409/88 |
| 954,447 | 4/1910 | Lyons | 409/85 X |
| 1,073,547 | 9/1913 | Tunes | 409/85 |
| 2,314,499 | 3/1943 | Howard | 409/85 |
| 3,838,623 | 10/1974 | Schell | 409/104 |
| 4,842,454 | 6/1989 | Gustavsson et al. | 409/84 |
| 4,863,318 | 9/1989 | Pearl | 409/89 |

FOREIGN PATENT DOCUMENTS 144154 12/1935 Fed. Rep. of Germany ........ 409/85
187399 12/1887 France ................................. 409/85

Primary Examiner—William Briggs
Attorney, Agent, or Firm—Pollock, Vande Sande & Priddy

[57] ABSTRACT

The invention makes it possible to produce from a blank an article whose contour is altered, preferably linearly enlarged, with great precision in relation to a corresponding contour of a used model (1c). A copying machine is used in the production. The machine comprises, on the one hand, a first pair of units (1, 2) which are arranged so as to be rotatable. The model (1c) is arranged on the first unit (1) and the blank is arranged on the second unit (2). The machine also comprises a pair of second units (24, 25) in which one supports a detecting member (24a) which is brought into cooperation with the model, and the second unit supports a machining or actuating member which is brought into cooperation with and acts on the blank. The said pairs of units are displaced from and towards each other during production. In each pair of units, the units are also controlled individually so that the one unit executes second displacement movements relative to the other unit in such a way that the desired alteration is obtained.

7 Claims, 3 Drawing Sheets

COPYING METHOD AND DEVICE

FIELD OF THE INVENTION

The present invention relates to a method and device for producing an article from a blank, the contour of the article being altered or enlarged, with great precision in relation to a corresponding contour of a used model. The method is used in a copying machine which has a first and a second pair of units. The units of the first pair are arranged to be rotatable. The model is arranged on the first unit in the first pair, and the blank is arranged on the second unit. The one unit in the second pair of units supports a detecting member which is brought into cooperation with the model, and the other unit in the second pair supports a machining or actuating member which is brought into cooperation with and acts upon the blank. During production the pairs of units execute relative first displacement movements towards and away from each other during production of the article. The invention also relates to a device (copying mill machine) by means of which the new method is made possible.

BACKGROUND OF THE INVENTION

The present invention represents a further development of the copying machine according to Swedish Patent 8601870-2. Individually shaped articles of different types can be produced using this machine. The machine is particularly advantageous for the production of, for example, insertion articles for artificial construction of teeth, human joints, and the like. The machine is also suitable, in an intermediate stage in the production of tooth crowns or other cap-shaped articles, for producing tools in the form of electrodes, press tools, and the like with the desired contour for the finished product or machined article.

In the production it may be of interest to produce articles, tools and the like with high precision and in a technically simple manner. In conjunction with the production of, for example, ceramic tooth crowns, it is necessary to produce a tool, for example press tool, for the ceramic material. It is desirable for the tool to be made with an outer contour which is enlarged in relation to the outer contour of the used model. There are cases in which it is desirable for the enlargement to be effected as far as possible linearly. This requirement is due to the fact that the ceramic material applied to the tool is to be subjected to hard sintering which causes a linear shrinking of the ceramic cap produced with the press tool. An absolute precondition for a good final result is that the linear enlargement/alteration must be carried out with great precision, for example $5 \times 10^{-6}$m. It is thus important that each length and radius of the model can be enlarged by a desired percentage with great precision. There are also cases in which the alteration/enlargement is required in only one direction of the axial and radial directions.

SUMMARY OF THE INVENTION

The purpose of the present invention is to provide a device (copying machine) and a method for use in the copying machine which solve, among other things, the problems mentioned above.

The feature which can be regarded principally as characterizing the new method is that the two units in one or both pairs of units are caused to execute second displacement movements relative to each other in addition to the first displacement movement giving the desired alteration or enlargement.

The feature which can be regarded principally as characterizing the new device is that, during the production, the units in the first and/or second pair of units are arranged to execute second displacement movements relative to each other which give the alteration/enlargement.

In one preferred embodiment first and second linkage systems are used by means of which one unit is mechanically controlled in relation to the other unit in each pair of units. The copying machine is also designed in such a way that it is possible to manually adjust the percentage value by which the enlargement is to be carried out.

In a second embodiment the first and second pairs of units are arranged at an obtuse angle with respect to each other, such that the relative displacement between the units of the first pair effects the alteration or enlargement in the longitudinal direction of the model/article, and the relative displacement between the units of the second pair effects the alteration or enlargement in the radial direction of the model/article.

The invention provides, among other things, a method and device for replacing lost tooth substance with various materials which are biocompatible, such as for example ceramic material. The procedure can include the production of tools, for example press tools, which will form part of a mold in which the material will be applied. In the subsequent treatment of the material, the article, for example the cap produced in the mold is shrunk, which means that the contour transferred from the starting model of the cap or corresponding model to the tool in the copying machine must be enlarged linearly with great precision so that the article produced by means of the tool can be shrunk to dimensions which match the corresponding dimensions of the model with a great degree of accuracy. By means of the invention, the great accuracy required can be achieved in a linear enlargement. The invention also permits the production of linearly enlarged, individually shaped articles.

A proposed embodiment of a method and a device according to the invention will be described below with reference to the attached drawings, in which

DETAILED DESCRIPTION OF THE PREFERRED EMBODIMENT(S)

The new copying machine is a further development of the machine disclosed in the Swedish Patent 8601870-2, and therefore only those parts directly relevant to the present invention will be described here.

Figure 1:
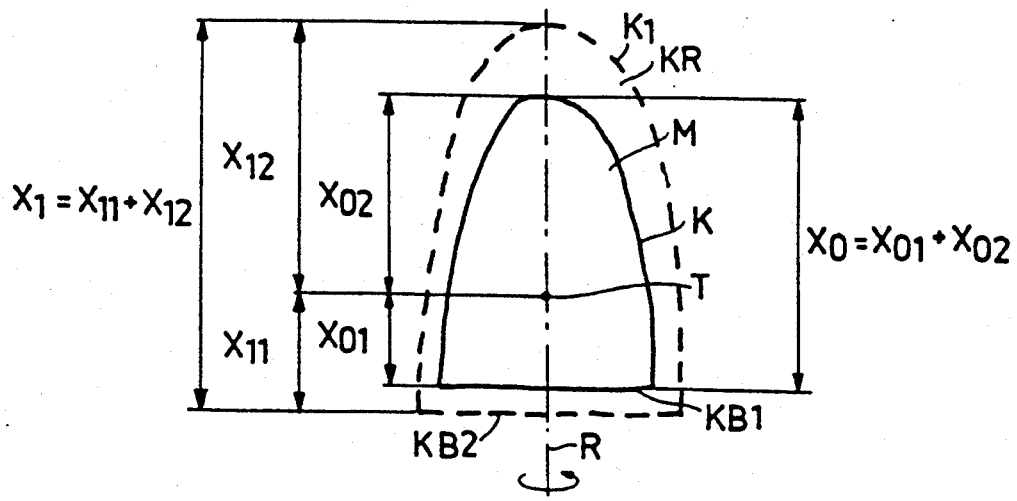
FIG. 1 shows, in a vertical view, an example of the outer contour of a copyable article which is enlarged linearly in the axial direction.

FIG. 1 shows with a full line a model M whose outer contour K is to be enlarged linearly in the axial direction. The enlarged article KR is shown with a broken line, and the contour of the enlarged article is indicated by K1. Linear enlargement here means that each length of the model is enlarged by a percentage value which, in one embodiment of the machine, can be selected in an adjustable manner. The center of gravity is shown by T and the axis of rotation by R, for which a rotation arrow is also indicated.

The following relationship applies in FIG. 1:

$$\begin{array}{r} x_{01} \cdot f = x_{11} \\ x_{02} \cdot f = x_{12} \\ \hline (x_{01} + x_{02}) \cdot f = x_{11} + x_{12} \\ x_0 \cdot f = x_1; \end{array}$$

in which f is the enlargement factor.

Figure 1A:
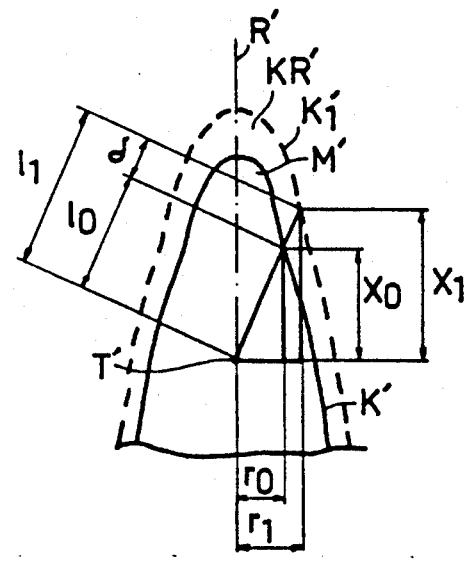
FIG. 1a shows, in a vertical view, an example of the outer contour of an article enlarged in the radial direction.

FIG. 1a corresponds to the case in which the linear enlargement is effected in the copying machine according to the invention in the radial direction. The references in FIGS. 1 and 1a correspond to each other, and in FIG. 1a they have been supplemented with primes. For the enlargement according to FIG. 1a the following relationship applies:

$$\frac{r_0}{l_0} = \frac{r_1}{l_1} = \frac{r_0 \cdot f}{l_0 \cdot f} ; \text{ and } \frac{x_0}{l_0} = \frac{x_1}{l_1} = \frac{x_0 \cdot f}{l_0 \cdot f} ;$$

in which f is the enlargement factor.

From the uniform triangles obtained in FIG. 1a it emerges that if $l_0$ is enlarged or $l_0$ shrinks a distance $\delta$ proportional to $l_0$ or $l_1$, r and x are altered in the same proportion. In this respect it is assumed that the center line of rotation R' passes through the center of gravity T'.

There may be problems in determining exactly the position of the center of gravity T, T', which means that the article can be rotated about an axis which deviates from the central axis of rotation R, R'. However, it is found in practice that deviations in this respect are of no importance as regards the result obtained. The new machine and the new method for production using the machine still give the desired result that is accuracy of about 5 μm).

In the copying machine the linear enlargement starts from a fixed back plane, see KB1 and KB2 in FIG. 1. This too has no importance in a practical case where one can start from the fact that an axial percentage enlargement or shrinkage with respect to a section through the center of gravity gives the same result as an axial enlargement or shrinkage with respect to any other section at right angles to the center line. Even if the axial position of the article depends on from which section the enlargement is calculated, this is of no importance in the copying. In one preferred embodiment each length and each radius of the model are enlarged by a percentage.

Figure 2:
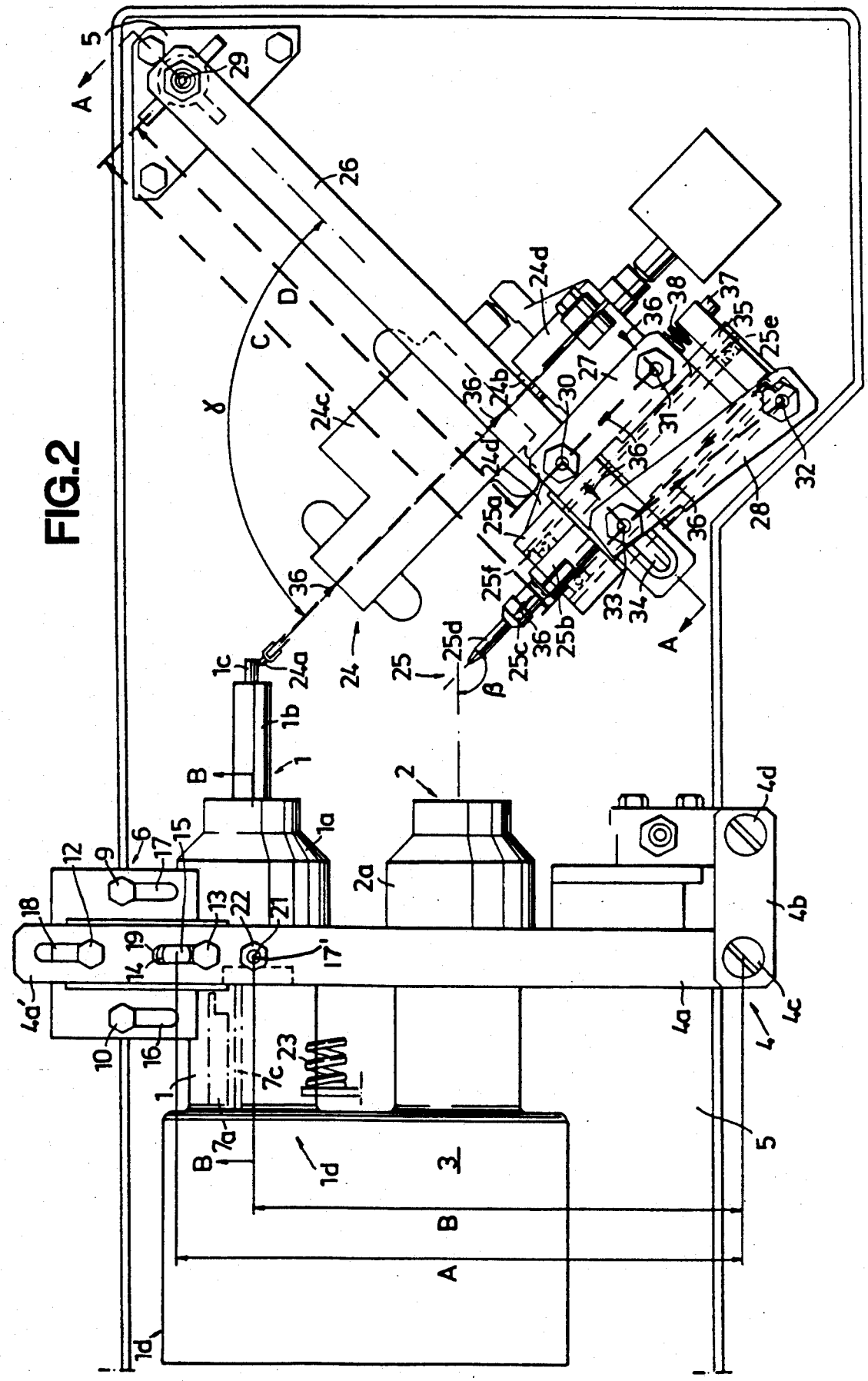
FIG. 2 is a plan view of parts included in a copying machine according to the present invention.

The machine according to FIG. 2 comprises a first pair of units in which the first unit has been indicated by 1 and the second unit by 2. The units are rotatably arranged in a housing 3 which is displaceable in the longitudinal direction of the units. The unit 1 is provided with a chuck/securing device 1a in which a holder 1b which supports a model (replica) 1c can be secured. The second unit 2 comprises a chuck/securing device 2a in which a holder for a blank can be secured or attached in a corresponding manner. The unit 1 is displaceable relative to the housing 3 in combined bearing and driving members 1d.

Figure 3:
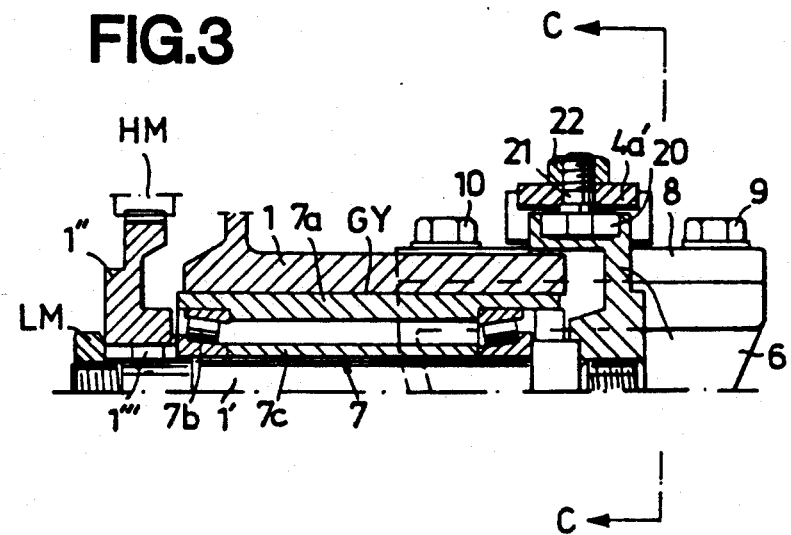
FIG. 3 is a cross-section along the cut line B—B in FIG. 2.
Figure 4:
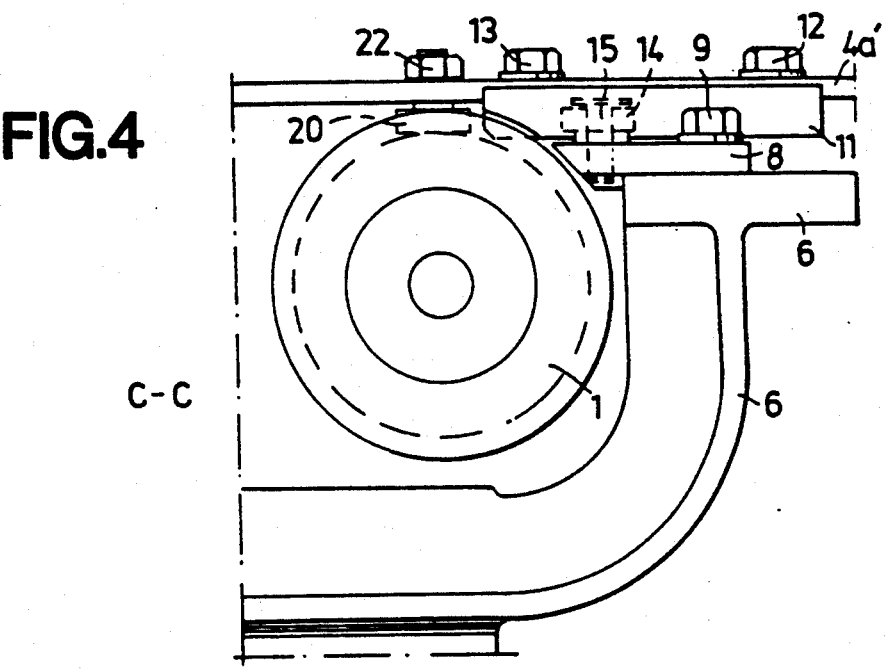
FIG. 4 is a side view according to C—C in FIG. 3.
Figure 5:
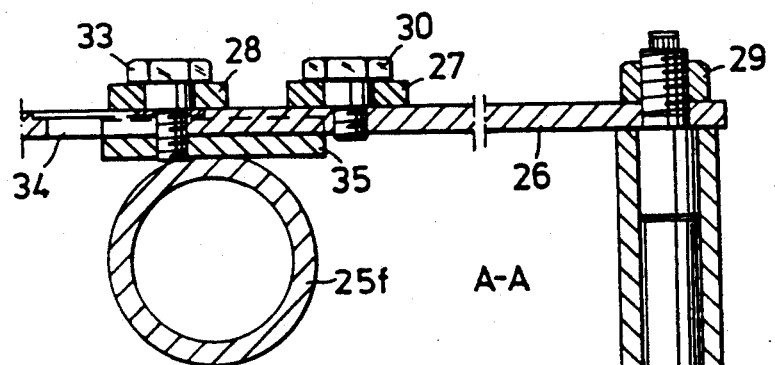
FIG. 5 is a cross-section along the cut line A—A in FIG. 2.
Figure 6:
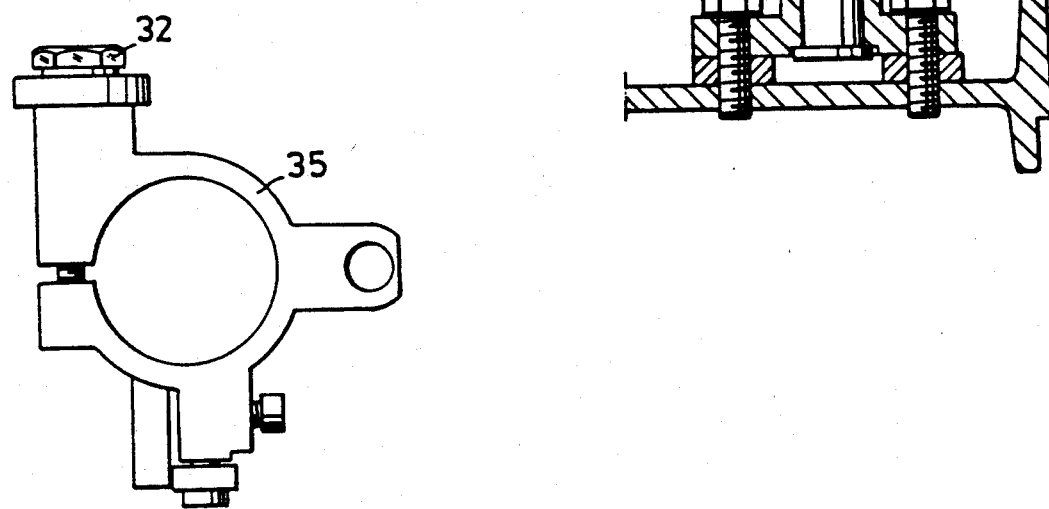
FIG. 6 is an end view of a bearing unit arranged on a tool spindle included in the copying machine.

In addition to its longitudinal displacement movement via the longitudinally displaceable housing 3 which can be considered as a first longitudinal displacement, the unit 1 is also controlled mechanically by an outer first linkage system 4 by means of which the first unit is braked relative to the second unit, which can then be regarded as a second longitudinal displacement movement or enlargement movement relative to the unit 1, in such a way that the percentage enlargement in the axial direction according to FIG. 1a is obtained. The linkage system 4 comprises a first link arm 4a and a second link arm 4b. The arms are rotatably mounted relative to each other in a bearing 4c, and the bearing point for the linkage system in the body 5 is indicated by 4d. The arm 4a extends across the units 1 and 2 to a bracket 6 (see also FIG. 4) which is designed to follow the longitudinal displacement movements of the housing 3. The end 4a' of the arm is mounted in the bracket in accordance with FIGS. 3 and 4. In FIG. 3 the rotatable axle of the unit 1 is indicated by 1'. The combined bearing and drive members 1d can also be seen. The axle 1' is mounted in a bearing part 7 which consists of a unit longitudinally displaceable in the body of the unit 1, with a non-rotating part 7a, and a part 7c rotatable in this via bearing 7b. The axial slide surface between the body 1 and the part 7a is indicated by GY. The unit also comprises a drive wheel 1'' which is rotatably anchored to the axle 1' via a wedge 1'''. The drive wheel 1'' is driven by a drive member HM, for example a hydraulic motor. The gear engagement between the wheel 1'' and the drive member HM permits relative longitudinal displacement with retention of the gear engagement. A tightening nut LM is arranged at one end of the axle 1''. At the other end of the axle 1' there is a securing part 1e for the chuck 1a of the unit 1. The part 1e is secured via a thread on the axle and has, in a known manner, screw holes for the chuck. Secured on the top surface of the bracket there is a plate 8 which is held in the bracket by means of screws 9, 10. On the underside of the arm end 4a' there is an actuating part 11 for the arm end (see FIG. 4). The actuating part is secured by means of screws 12, 13. The movement of the bracket is transferred to the arm end 4a' by means of a ball bearing 14 which is anchored in a holder part 15 screwed into the plate 8. The ball bearing is arranged in a recess in the actuating part 11.

The center distance between the holder part 15 and the bearing points 4c for the link arms is indicated by A. The bearing 14 can, in accordance with FIG. 4, be displaced by first loosening the screws 9, 10 and 12, 13 and then, on the one hand, displacing the plate 8, see also the oblong holes 16, 17 in FIG. 2, and on the other hand displacing the part 11, see the oblong holes 18, 19 in FIG. 2.

The movement thus transferred from the bracket to the link arm 4a is conveyed further to the unit 1 via a ball bearing 20 arranged in a part 1e projecting from the unit 1. The bearing 21 of the ball bearing is secured in the link arm by means of a nut 22 which is screwed tight on a thread in the part 21. By means of this arrangement, unit 1, in its longitudinal direction, is braked in its movement relative to the second unit 2. The second unit can therefore be regarded as executing a second displacement movement or additional movement in relation to the unit 1. The unit 2 thus does not cooperate with the link arm 4a. A distance between the bearing 4c of the link 4a and the bearing 17' for the working point of the link arm in the unit 1 is indicated by B. The enlarged movement (enlargement f) for the first unit is determined by the distance relationship A/B (thus equal f), which can be adjusted according to the above. The arrangement for mechanical control of the unit 1 ensures that alteration or enlargement is effected in the copied article (can consist of a tool) in respect of its longitudinal direction.

The link arm 4a can be acted upon by a spring 23 which is designed to compensate for any play in the transmission system of the linkage. The arrangement with the link arms 4a, 4b and intermediate bearing 4c also means that a certain minor adjustment can be made to the movement of the link arm 4 when the bracket 6 moves parallel to the direction of movement of the unit 1.

The copying machine has a second pair of units which are here referred to as the third unit 24 and the fourth unit 25. The third unit comprises a member (needle) 24a which is longitudinally displaceable and senses the contour of the model 1c. In a known manner the member or needle controls a servo piston 24b which, together with the bearing, is mounted in a bearing housing 24c. The servo piston/rod supports a bearing part 24d for the fourth unit 25. The latter comprises a spindle housing 25a which is secured to the bearing part 24d via an attachment 24'on the latter. The fourth unit also comprises a chuck 25c for securing a tool 25d (cutter, laser, and the like). The spindle part 25b is mounted via a bearing (ball bearing) 25e in a sleeve 25f which is longitudinally displaceable in the spindle housing 25a. Via the ball bearing 25e the spindle part 25b is, on the one hand, arranged rotatable relative to the sleeve 25f and, on the other hand, fixed in the longitudinal direction of the sleeve in such a way that the spindle part 25b, and thus the tool 25d, is longitudinally displaceable by means of the sleeve relative to the spindle housing 25a and the part 24d. The chuck 25c can be secured in the spindle part.

The member 24a and the tool 25d are directed towards the model and blank, respectively, at an obtuse angle $\beta$ which lies within the range of 110°-180°, and is preferably about 135°.

The longitudinally displaceable sleeve 25f in the spindle housing is controlled mechanically by means of a second linkage system which comprises link arms 26, 27 and 28. Link arm 26 is mounted at point 29 on the body part 30a and extends across the parallel units 24, 25.

The link arms are joined by means of screws 30, 31, 32 and 33. Screw 30 is mounted in link 27 and is securely screwed in link 26. Screw 31 is mounted in link 27 and securely screwed at 24d (24d'). Screw 33 is mounted in link 28 and is securely screwed in link 26. Screw 33 can be securely screwed at any chosen position along the groove 34 in link 26. Screw 32 is mounted in link 28 and is securely screwed in a unit 35 which is securely clamped on the sleeve 25f.

The movement from the detecting member 24a follows the broken line shown by arrows 36 to the member 25d when the member 24a moves a certain distance. This results in a movement of the screw (bearing) 30, which results in the link 26 moving a corresponding angular distance about the point 29. The screw (bearing) 33 (i.e. the sleeve 25f) thus moves a distance which is C/D greater than the distance which 30 moves, where C is the distance between the bearing 29 and 33 and D is the distance between the bearings 29 and 30. The enlargement f is thus identical to C/D.

An adjustability of the percentage by which the enlargement is to take place is afforded by the arrangement of the recess 34, in which the bearing point 33 is displaceable for variation of the distance C. An alteration of the distance C results in an alteration of the initial displacement position between the member 24c and the part 25d.

The chosen adjustment possibility for the enlargement f (percentage by which enlargement is to take place) has been chosen in this example between 16 and 25%. The machine can of course be designed with other adjustment ranges. The bearing member 35 is held by a pin 37 arranged in the bearing part 24d. A spring 38 between the bearing part 24d and an inner surface of the bearing member 35 is designed to eliminate any play in the linkage system. An angle $\gamma$ between the longitudinal axis of the unit 24 and the longitudinal axis of the link arm 26 is preferably about 90° when the tool/member 25d assumes an intermediate position. The arrangement with the second linkage system provides for enlargement in the radial direction of the produced article.

In each pair of units the one unit is thus arranged longitudinally displaceable relative to the other unit. The one pair of units is thus concerned with the linear enlargement in the longitudinal direction of the article, and the other pair of units is concerned with the enlargement in the radial direction of the article. In one embodiment, only one of the pairs of units need be designed with relative displaceability between the units. The relative movement between the units in each pair of units can also be adjustable, individually or in coordination, to the same or different percentage of values enlargement. Each additional movement can be effected by means of members effecting the additional movement which can have the form of one or more link arms, electric motors, hydraulic control, and the like.

The invention is not limited to the above preferred embodiment, but instead can be modified in accordance with the following patent claims and the inventive concept.

We claim:

1. A method for producing an article from a blank, the contour of the article being altered with respect to a selected model by using a copying machine including a first pair of units having a first unit for supporting the model and a second unit for supporting the blank and a second pair of units including a third unit for supporting a detecting member, and a fourth unit for supporting a machining member, said method comprising the steps of:
   1) controlling said units of said first and second pair for execution of first relative longitudinal displacement movements of said pairs of units towards and way from each other such that said detecting member is brought in cooperation with the model for detecting its contour and the machining member is brought into contact for working upon the blank;
   2) controlling one of said first and second units in said first pair by a first linkage system associated with said first pair such that the other of said first and second units executes second displacement movements with respect to the one unit to provide a desired alteration of the article contour in the longitudinal direction;

3) controlling one of said third and fourth units in said second pair by a second linkage system associated with said second pair such that the other of said third and fourth units executes second displacement movements with respect to the one unit to provide a desired alteration of the article contour in the radial direction; and 4) wherein said units are positioned such that longitudinal axes of said first and third unit relative to said second and fourth unit respectively are at an angle with respect to each other.

2. A system for producing an article from a blank, the contour of the article being altered with respect to a selected model by using a copying machine including:

a first pair of units having a first unit for supporting the model and a second unit for supporting the blank and a second pair of units including a third unit for supporting a detecting member, and a fourth unit for supporting a machining member;

means for controlling said units of said first and second pair for execution of first relative longitudinal displacement movements of said pairs of units towards and way from each other such that said detecting member is brought in cooperation with the model for detecting its contour and the machining member is brought into contact for working upon the blank;

a first linkage system associated with said first pair for controlling one of said first and second units in said first pair such that the other of said first and second units executes second displacement movements with respect to the one unit to provide a desired alteration of the article contour in the longitudinal direction;

a second linkage system associated with said second pair for controlling one of said third and fourth units in said second pair such that the other of said third and fourth units executes second displacement movements with respect to the one unit to provide a desired alteration of the article contour in the radial direction; and wherein said units are positioned such that longitudinal axes of said first and third unit relative to said second and fourth unit respectively are at an angle with respect to each other.

3. Device according to claim 2 wherein in said first and second pair of units one unit is longitudinally displaceable relative to the other unit, and wherein the unit in the first pair of units which executes the second longitudinal displacement cooperates with the unit in the second pair of units which does not execute the second longitudinal displacement movement, whereby the one pair of units is thus concerned with linear alternation in the longitudinal direction of the article, and the second pair is concerned with linear alternation in the radial direction of the article.

4. A device according to claim 2, wherein said first linkage system comprises a first link arm which is mounted at its one end and extends across and beyond said first and second units of said first pair which are arranged in parallel, and wherein at a projecting part of said first link arm manually actuatable adjustment members are provided for manual adjustment of the relative displaceability between the first and second unit of the first pair of units.

5. A device according to claim 4, wherein said manually actuatable members are mounted on a bracket which follows the movements of the bearing housing in the longitudinal direction of said first and second units of said first pair of units, and wherein connecting members are arranged between said bracket and said first link arm whose movements transferred from the bracket are being passed to one of said first and second units of the first pair.

6. A system for producing an article from a blank, the contour of the article being altered with respect to a selected model by using a copying machine including:

a first pair of units having a first unit for supporting the model and a second unit for supporting the blank and a second pair of units including a third unit for supporting a detecting member, and a fourth unit for supporting a machining member, said units being positioned such that longitudinal axes of said first and third unit and said second and fourth unit respectively are at an angle with respect to each other;

means for controlling said units of said first and second pair for execution of first relative longitudinal displacement movements of said pairs of units towards and way from each other such that said detecting member is brought in cooperation with the model for detecting its contour and the machining member is brought into contact for working upon the blank;

a linkage system associated with said first pair for controlling one of said first and second units in said first pair such that the other of said first and second units executes second displacement movements with respect to the one unit to provide a desired alteration of the article contour in the longitudinal direction;

a second linkage system associated with said second pair for controlling one of said third and fourth units in said second pair such that the other of said third and fourth units executes second displacement movement with respect to the one unit to provide a desired alteration of the article contour in the radial direction;

said second linkage system comprising a second link arm which is mounted at a fixed point and extends across said third and fourth units of said second pair which are arranged in parallel, said second link arm at its free end being provided with manually actuatable adjustment members for manual adjustment of a percentage value of the second displacement movements of the said second pair of units, and wherein the link arms of the second linkage system comprise further links for transferring movements from the one unit of the second pair to the other unit.

7. Device according to claim 2, wherein the second linkage system comprises a second link arm which is mounted at a fixed point and extends across the units of the second pair which are arranged in parallel, said second link arm at its free end being provided with manually actuatable adjustment members for manual adjustment of a percentage value of the second displacement movements of the said second pair of units, and wherein the link arms of the second linkage system comprise further links for transferring movements from the one unit of the second pair to the other unit.

* * * * *